United States Patent
Klein et al.

(10) Patent No.: US 9,080,183 B2
(45) Date of Patent: Jul. 14, 2015

(54) PROMOTER

(75) Inventors: Christian Klein, Iffeldorf (DE); Erhard Kopetzki, Penzberg (DE)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 617 days.

(21) Appl. No.: 12/664,399

(22) PCT Filed: Jun. 25, 2008

(86) PCT No.: PCT/EP2008/005135
§ 371 (c)(1),
(2), (4) Date: Dec. 14, 2009

(87) PCT Pub. No.: WO2009/003622
PCT Pub. Date: Jan. 8, 2009

(65) Prior Publication Data
US 2010/0159489 A1    Jun. 24, 2010

(30) Foreign Application Priority Data

Jun. 29, 2007 (EP) .................................. 07012772

(51) Int. Cl.
*C12N 15/00* (2006.01)
*C12N 15/85* (2006.01)
*C07K 14/47* (2006.01)

(52) U.S. Cl.
CPC ............ *C12N 15/85* (2013.01); *C07K 14/4702* (2013.01)

(58) Field of Classification Search
None
See application file for complete search history.

(56) References Cited

U.S. PATENT DOCUMENTS

2009/0041783 A1 * 2/2009 Takayama et al. ......... 424/172.1

FOREIGN PATENT DOCUMENTS

| JP | 2006-050956 | 2/2006 |
| WO | WO 9962927 | 12/1999 |

OTHER PUBLICATIONS

Hartzell, S.W. et al., Proc. Natl. Acad. Sci 81:23-27 ( 1984).
(Translation of Korean Office Action 2009-70270412011).
(NCBI, GenBank, Accession No. EF550208.1 May 23,2007).
(Translation of Jap Off Act in Corres Jap Appl 2010513746 May 10, 2012).
Osamu Kanemitsu, Introduction to Antibody Engineering (Chijin Shokan Co., Ltd.),:198-201 (Jan. 25, 1994).
(Translation of Russian Off Act in Corres Appl 2010102812 Feb. 2, 2012).
Fromm M. et al: *Journal of Molecular and Applied Genetics*, vol. 1:5, (1982), pp. 457-481, XP008083910.
Fromm M. et al: *Journal of Molecular and Applied Genetics*, vol. 2:1, (1983), pp. 127-135, XP008083908.
Gorman C et al, *Molecular and Cellular Biology*, 2:9 (1982) 1044-105 XP000574017.
Dynan W et al, *Cll*, 35:1 (1983) 79-88 XP002451926.
Benoist C et al, *Nature*, 290:5804 (1981) 304-310 XP008083948.
Rio D et al, *Journal of Molecular and Applied Genetics*, 2:5 (1984) 423-435 XP008083924.
Everett R et al, *Nucleic Acids Research* 11:8 (1983) 2447-2464.
Firak T et al *Molecular and Cellular Biology*, 6:11, (1986) 3667-3676 XP002495690.
Gong, S et al, *Virology* 163:2 (1988) 481-493.

* cited by examiner

*Primary Examiner* — Celine Qian

(57) ABSTRACT

The current invention reports a promoter having the nucleic acid sequence of SEQ ID NO: 02, or SEQ ID NO: 03, or SEQ ID NO: 04, or SEQ ID NO: 06, which is a 5' shortened SV40 promoter with reduced promoter strength especially useful for the limited expression of heterologous polypeptides or selectable markers.

9 Claims, 7 Drawing Sheets

PROMOTER

This application is the National Stage of International Application No. PCT/EP2008/005135 filed Jun. 25, 2008, which claims the benefit of EP 07012772.5 filed Jun. 29, 2007, which is hereby incorporated by reference in its entirety.

The current invention is in the field of protein expression and cell selection. It is herein reported a promoter with low promoter strength and thus with a limited expression of an operably linked coding nucleic acid.

BACKGROUND OF THE INVENTION

The expression of proteins is a fundamental process in living cells. All information required for protein expression is provided by a single nucleic acid. This nucleic acid not only contains the information of the protein's amino acid sequence, it also provides the regulatory information required (e.g. the ribosomal binding site, the start and end-signals for transcription, splice signals, enhancer elements, etc.) including a promoter/promoter sequence.

A promoter is a nucleic acid that regulates the amount of transcription of a nucleic acid, e.g. encoding a polypeptide, to which it is operably linked, into pre-mRNA. It is a transcription control element, which is located around the RNA polymerase initiation site at the 5'-end of an operably linked coding sequence. From analysis of the SV40 early promoter it is known that recognition/binding sites for transcription activators are contained in promoters in segments consisting of 7-20 basepairs. One segment is the start site for RNA synthesis, e.g. the well known TATA-box. Other segments, located approximately 30-110 basepairs 5', i.e. upstream, to the start site for RNA synthesis, are defining the frequency of transcription initiation. A promoter at least requires one segment that initiates RNA synthesis at a specific site and in a defined direction, i.e. in 5' to 3' direction.

Known promoters are the lac-lpp, the ara-, the lac-, the tac-, the trc-, the trp-, the phoA-, the $P_{BAD}$-, the $\lambda_{PL}$-, the lpp-, and the T7-promoter. The SV40 promoter is a nucleic acid sequence derived from the genome of Simian (vacuolating) Virus 40. For the recombinant production of a heterologous polypeptide in a eukaryotic or prokaryotic cell normally one or more expression plasmids are introduced into the cell. The expression plasmid(s) comprises an expression cassette for the expression of a heterologous polypeptide and also an expression cassette for the expression of a selectable marker, which is required for the selection of transfected cells expressing the heterologous polypeptide. The synthesis of the heterologous polypeptide and of the selectable marker both requires a fraction of the cell's expression machinery's capacity.

As it is the aim to produce predominantly the heterologous polypeptide most of the available capacity of the cell's expression machinery should be allocated to the expression of the nucleic acid encoding the heterologous polypeptide. Only a minor amount should be used for the expression of the selectable marker. This allocation of expression capacity is done via the strength of the corresponding promoters. The stronger a promoter is the more of the operably linked nucleic acid is transcribed and thus translated. Therefore, it exists a need for promoters with adjustable or reducible promoter strength.

Taylor, W. E., et al. (Endocrinol. 137 (1996) 5407-5414) report human stem cell factor promoter deletion variants. In US patent application US 2007/0092968 novel hTMC promoter and vectors for the tumor-selective and high-efficient expression of cancer therapeutic genes is reported. Fromm et al. (J. Mol. Appl. Gen. 1 (1982) 457-481 and ibid 2 (1983) 127-135) report deletion mapping and deletion mutants of SV-40 early region promoter. Chitinase chitin-binding fragments are reported in U.S. Pat. No. 6,399,571. WO 99/62927 reports connective tissue growth factor-4.

SUMMARY OF THE INVENTION

The first aspect of the current invention is a promoter having, i.e. with, a nucleic acid sequence of SEQ ID NO: 02 or SEQ ID NO: 03 or SEQ ID NO: 04 or SEQ ID NO: 06. In one embodiment the promoter has the nucleic acid sequence of SEQ ID NO: 04.

A second aspect of the current invention is a nucleic acid that has the nucleotide sequence of SEQ ID NO: 04 and that has a promoter strength of 20% or less compared to the wild-type SV40 promoter of SEQ ID NO: 05 when operably linked to the nucleic acid sequence of SEQ ID NO: 07 encoding the green-fluorescent-protein (GFP).

A further aspect of the current invention is a method for the selection of a cell comprising the following steps in this order:
a) transfecting a eukaryotic cell with a nucleic acid comprising
  i) a first expression cassette comprising a nucleic acid encoding a heterologous polypeptide,
  ii) a second expression cassette comprising a first nucleic acid of SEQ ID NO: 04 and a second nucleic acid encoding a selectable marker, whereby the first nucleic acid is operably linked to the second nucleic acid,
b) cultivating said transfected cell under conditions suitable for growth of the non-transfected eukaryotic cell,
c) selecting a cell propagating in step b) and also
  i) propagating under selective culture conditions, or
  ii) expressing the selectable marker.

In one embodiment of this aspect of the invention the eukaryotic cell is a mammalian cell. In a preferred embodiment the mammalian cell is a CHO cell, BHK cell, or PER.C6® cell, or HEK cell, or Sp2/0 cell. In another embodiment the heterologous polypeptide is an immunoglobulin, or an immunoglobulin-fragment, or an immunoglobulin-conjugate. In one embodiment the selectable marker is a neomycin-aminoglycoside phosphotransferase, or a hygromycin-phosphotransferase, or dLNGFR, or GFP.

A forth aspect of the current invention is a method for the expression of a heterologous polypeptide which comprises the following steps in this order:
a) transfecting a mammalian cell with a nucleic acid comprising an expression cassette comprising a first nucleic acid of SEQ ID NO: 02 or SEQ ID NO: 03 or SEQ ID NO: 04 or SEQ ID NO: 06 operably linked to a second nucleic acid encoding a heterologous polypeptide,
b) selecting a cell transfected in step a),
c) cultivating the selected cell under conditions suitable for the expression of the heterologous polypeptide,
d) recovering the heterologous polypeptide from the cell or the cultivation medium.

In one embodiment of this aspect of the current invention the mammalian cell is a CHO cell, a BHK cell, or a PER.C6® cell, or HEK cell, or Sp2/0 cell. In another embodiment the first nucleic acid is of SEQ ID NO: 04. In a further embodiment the second nucleic acid is encoding an immunoglobulin, or an immunoglobulin-fragment, or an immunoglobulin-conjugate. In still another embodiment the nucleic acid comprises a second expression cassette encoding a selectable marker.

DETAILED DESCRIPTION OF THE INVENTION

The current invention reports a novel promoter nucleic acid with a nucleotide sequence of SEQ ID NO: 02, or SEQ ID NO: 03, or SEQ ID NO: 04, or SEQ ID NO: 06.

Methods and techniques useful for carrying out the current invention are known to a person skilled in the art and are described e.g. in Ausubel, F. M., ed., Current Protocols in Molecular Biology, Volumes I to III (1997), and Sambrook, et al., Molecular Cloning: A Laboratory Manual, Second Edition, Cold Spring Harbor Laboratory Press, Cold Spring Harbor, N.Y. (1989). As known to a person skilled in the art enables the use of recombinant DNA technology the production of numerous derivatives of a nucleic acid and/or polypeptide. Such derivatives can, for example, be modified in one individual or several positions by substitution, alteration, exchange, deletion, or insertion. The modification or derivatisation can, for example, be carried out by means of site directed mutagenesis. Such modifications can easily be carried out by a person skilled in the art (see e.g. Sambrook, J., et al., Molecular Cloning: A laboratory manual (1999) Cold Spring Harbor Laboratory Press, New York, USA). The use of recombinant technology enables a person skilled in the art to transform various host cells with heterologous nucleic acid(s).

A "promoter" refers to a nucleic acid, i.e. polynucleotide sequence, which controls transcription of a nucleic acid to which it is operably linked. A promoter may include signals for RNA polymerase binding and transcription initiation. The promoter(s) used will be functionable in the cell type of the host cell in which expression of the operably linked nucleic acid is contemplated. A large number of promoters including constitutive, inducible, and repressible promoters from a variety of different sources are well known in the art (and identified in databases such as GenBank). They are available as or within cloned polynucleotides (from, e.g., depositories such as ATCC as well as other commercial or individual sources). A "promoter" comprises a nucleotide sequence that directs the transcription of e.g. an operably linked structural gene. Typically, a promoter is located in the 5' non-coding or 5'-untranslated region (5'UTR) of a gene, proximal to the transcriptional start site of a structural gene. Sequence elements within promoters that function in the initiation of transcription are often characterized by consensus nucleotide sequences. These sequence elements include RNA polymerase binding sites, TATA sequences, CAAT sequences, differentiation-specific elements (DSEs; McGehee, R. E., et al., Mol. Endocrinol. 7 (1993) 551), cyclic AMP response elements (CREs), serum response elements (SREs; Treisman, R., Seminars in Cancer Biol. 1 (1990) 47), glucocorticoid response elements (GREs), and binding sites for other transcription factors, such as CRE/ATF (O'Reilly, M. A., et al., J. Biol. Chem. 267 (1992) 19938), AP2 (Ye, J., et al., J. Biol. Chem. 269 (1994) 25728), SP1, cAMP response element binding protein (CREB; Loeken, M. R., Gene Expr. 3 (1993) 253-264) and octamer factors (see, in general, Watson et al., eds., Molecular Biology of the Gene, 4th ed., The Benjamin/Cummings Publishing Company, Inc. 1987, and Lemaigre, F. P. and Rousseau, G. G., Biochem. J. 303 (1994) 1-14). If a promoter is an inducible promoter, then the rate of transcription increases in response to an inducing agent. In contrast, the rate of transcription is not regulated by an inducing agent if the promoter is a constitutive promoter. Repressible promoters are also known. For example, the c-fos promoter is specifically activated upon binding of growth hormone to its receptor on the cell surface. Tetracycline (tet) regulated expression can be achieved by artificial hybrid promoters that consist e.g. of a CMV promoter followed by two Tet-operator sites. The Tet-repressor binds to the two Tet-operator sites and blocks transcription. Upon addition of the inducer tetracycline, the Tet-repressor is released from the Tet-operator sites and transcription proceeds (Gossen, M. and Bujard, H., Proc. Natl. Acad. Sci. USA 89 (1992) 5547-5551). For other inducible promoters including metallothionein and heat shock promoters, see, e.g., Sambrook, et al. (supra), and Gossen, M., et al., Curr. Opin. Biotech. 5 (1994) 516-520. Among the eukaryotic promoters that have been identified as strong promoters for high-level expression are the SV40 early promoter, adenovirus major late promoter, mouse metallothionein-I promoter, Rous sarcoma virus long terminal repeat, Chinese hamster elongation factor 1 alpha (CHEF-1, see e.g. U.S. Pat. No. 5,888,809), human EF-1 alpha, ubiquitin, and human cytomegalovirus immediate early promoter (CMV IE). An enhancer (i.e., a cis-acting DNA element that acts on a promoter to increase transcription) may be necessary to function in conjunction with the promoter to increase the level of expression obtained with a promoter alone, and may be included as a transcriptional regulatory element. Often, the polynucleotide segment containing the promoter will include enhancer sequences as well (e.g., CMV or SV40).

The term "nucleic acid" as used herein, is a polymer consisting of individual nucleotides, i.e. a polynucleotide. It refers to a naturally occurring, or partially or fully non-naturally occurring nucleic acid, which is e.g. encoding a polypeptide that can be produced recombinantly. The nucleic acid can be build up of DNA-fragments which are either isolated or synthesized by chemical means. The nucleic acid can be integrated into another nucleic acid, e.g. in an expression plasmid or the genome/chromosome of a host cell. Plasmid includes shuttle and expression vectors. Typically, the plasmid will also comprise a prokaryotic propagation unit comprising an origin of replication (e.g. the ColE1 origin of replication) and a selectable marker (e.g. ampicillin or tetracycline resistance gene) for replication and selection, respectively, of the vector in bacteria.

The term "promoter strength" and grammatical equivalents thereof as used within the current invention denotes the efficacy of a promoter in the transcription of an operably linked nucleic acid. The promoter strength of a promoter can be high, i.e. it can be of from 90% to more than 100%, or medium, i.e. it can be of from 40% to less than 90%, or low, i.e. it can be up to less than 40%, if compared to the promoter strength of the wild-type SV40 promoter of SEQ ID NO: 05. This value can be determined by comparing the amount of expression of a heterologous polypeptide operably linked to the promoter in question to the amount of expression of the heterologous polypeptide operably linked to the wild-type SV40 promoter in the same cell type. This can be done e.g. by determining the amount of expression of the heterologous polypeptide in a CHO- or HEK-cell transfected with an expression cassette consisting of the promoter in question operably linked to a nucleic acid encoding the heterologous polypeptide by an ELISA-assay. By comparing this amount to the amount of expression of the same heterologous polypeptide in the same cell line transfected with an expression cassette consisting of the wild-type SV40 promoter operably linked to a nucleic acid encoding the heterologous polypeptide determined with the same ELISA-assay i.e. comparing the amount of heterologous polypeptide in the same cell with the same expression plasmid wherein only the promoter is changed, the relative promoter strength can be determined. The term "wild-type SV40 promoter" as used within this application denotes a nucleic acid of SEQ ID NO: 05 which correspond to position 72-411 of the nucleic acid of SEQ ID NO: 01, which is the genome of the SV40.

"Operably linked" refers to a juxtaposition of two or more components, wherein the components so described are in a relationship permitting them to function in their intended manner. For example, a promoter and/or enhancer are operably linked to a coding sequence, if it acts in cis to control or modulate the transcription of the linked coding sequence. Generally, but not necessarily, the DNA sequences that are "operably linked" are contiguous and, where necessary to join two protein encoding regions such as a secretory leader/signal sequence and a polypeptide, contiguous and in reading frame. However, although an operably linked promoter is generally located upstream of the coding sequence, it is not necessarily contiguous with it. Enhancers do not have to be contiguous. An enhancer is operably linked to a coding sequence if the enhancer increases transcription of the coding sequence. Operably linked enhancers can be located upstream, within, or downstream of coding sequences, and at considerable distance from the promoter. A polyadenylation site is operably linked to a coding sequence if it is located at the downstream end of the coding sequence in such a way that transcription proceeds through the coding sequence into the polyadenylation sequence. Linking is accomplished by recombinant methods known in the art, e.g., using PCR methodology, and/or by ligation at convenient restriction sites. If convenient restriction sites do not exist, then synthetic oligonucleotide adaptors or linkers are used in accord with conventional practice.

Within the scope of the present invention, transfected cells may be obtained with substantially any kind of transfection method known in the art. For example, the nucleic acid may be introduced into the cells by means of electroporation or microinjection. Alternatively, lipofection reagents such as FuGENE 6 (Roche Diagnostics GmbH, Germany), X-tremeGENE (Roche Diagnostics GmbH, Germany), and LipofectAmine (Invitrogen Corp., USA) may be used. Still alternatively, the nucleic acid may be introduced into the cell by appropriate viral vector systems based on retroviruses, lentiviruses, adenoviruses, or adeno-associated viruses (Singer, O., Proc. Natl. Acad. Sci. USA 101 (2004) 5313-5314).

The term "cell" or "host cell" refers to a cell into which a nucleic acid, e.g. encoding a heterologous polypeptide or constituting an shRNA, can be or is introduced/transfected. Host cells include both prokaryotic cells, which are used for propagation of vectors/plasmids, and eukaryotic cells, which are used for the expression of the nucleic acid. In one embodiment the eukaryotic cells are mammalian cells. In another embodiment the mammalian host cell is selected from the mammalian cells comprising CHO cells (e.g. CHO K1 or CHO DG44), BHK cells, NS0 cells, SP2/0 cells, HEK 293 cells, HEK 293 EBNA cells, PER.C6 cells, and COS cells. In a further embodiment the mammalian cell is selected from the group comprising hybridoma, myeloma, and rodent cells. Myeloma cells comprise rat myeloma cells (e.g. YB2), and mouse myeloma cells (e.g. NS0, SP2/0). Polypeptides for use in pharmaceutical applications are in one embodiment produced in mammalian cells such as CHO cells, NS0 cells, Sp2/0 cells, COS cells, HEK cells, BHK cells, PER.C6® cells, or the like. For the fermentation of the host cell and thus for the expression of the polypeptide of interest a cultivation medium is used. Today CHO cells are widely used for the expression of pharmaceutical polypeptides, either at small scale in the laboratory or at large scale in production processes. Due to their wide distribution and use the characteristic properties and the genetic background of CHO cells is well known. Therefore, CHO cells are approved by regulatory authorities for the production of therapeutic proteins for application to human beings. In one embodiment the mammalian cell is a CHO cell.

An "expression cassette" refers to a nucleic acid that contains the elements necessary for expression and secretion of at least the contained structural gene in a host cell. A nucleic acid is likewise characterized by its sequence consisting of individual nucleotides or by the amino acid sequence encoded by the nucleic acid molecule.

A "gene" denotes a nucleic acid which is a segment e.g. on a chromosome or on a plasmid which can effect the expression of a peptide, polypeptide, or protein. Beside the coding region, i.e. the structural gene, a gene comprises other functional elements e.g. a signal sequence, promoter(s), introns, and/or terminators.

A "structural gene" denotes the region of a gene without a signal sequence, i.e. the coding region.

The term "expression" as used herein refers to transcription and/or translation occurring within a cell. The level of transcription of a desired product in a host cell can be determined on the basis of the amount of corresponding mRNA that is present in the cell. For example, mRNA transcribed from a selected nucleic acid can be quantitated by PCR or by Northern hybridization (see Sambrook, et al., Molecular Cloning: A Laboratory Manual, Cold Spring Harbor Laboratory Press (1989)). The protein encoded by a selected nucleic acid can be quantitated by various methods, e.g. by ELISA, by assaying for the biological activity of the protein, or by employing assays that are independent of such activity, such as Western blotting or radioimmunoassay, by using antibodies that recognize and bind to the protein (see Sambrook, et al., 1989, supra).

"Regulatory elements" as used herein, refer to nucleotide sequences present in cis, necessary for transcription and/or translation of the nucleic acid sequence encoding a polypeptide of interest. The transcriptional regulatory elements normally comprise a promoter upstream of the nucleic acid sequence to be expressed, transcriptional initiation and termination sites, and a polyadenylation signal sequence. The term "transcriptional initiation site" refers to the nucleotide in the nucleic acid corresponding to the first nucleotide incorporated into the primary transcript, i.e. the mRNA precursor; the transcriptional initiation site may overlap with the promoter sequence. The term "transcriptional termination site" refers to a nucleotide sequence normally represented at the 3' end of a gene of interest to be transcribed, that causes RNA polymerase to terminate transcription. The polyadenylation signal sequence, or poly-A addition signal provides the signal for the cleavage at a specific site at the 3' end of eukaryotic mRNA and the post-transcriptional addition in the nucleus of a sequence of about 100-200 adenine nucleotides (polyA tail) to the cleaved 3' end. The polyadenylation signal sequence may include the consensus sequence AATAAA located at about 10-30 nucleotides upstream from the site of cleavage.

A "polypeptide" is a polymer of amino acid residues joined by peptide bonds, whether produced naturally or synthetically. Polypeptides of less than about 20 amino acid residues may be referred to as "peptides." Polypeptides comprising two or more amino acid chains or comprising an amino acid chain of a length of 100 amino acids or more may be referred to as "proteins". A polypeptide or protein may also comprise non-peptidic components, such as carbohydrate groups or metal ions. Carbohydrates and other non-peptidic substituents may be added to a protein by the cell in which the protein is produced, and may vary with the type of cell. Proteins and polypeptides are defined herein in terms of their amino acid backbone structure; additions such as carbohydrate groups are generally not specified, but may be present nonetheless.

"Heterologous DNA" or "heterologous polypeptide" refers to a DNA molecule or a polypeptide, or a population of DNA molecules or a population of polypeptides, that do not exist naturally within a given host cell. DNA molecules heterologous to a particular host cell may contain DNA derived from the host cell species (i.e. endogenous DNA) so long as that host cell derived DNA is combined with non-host cell derived DNA (i.e. exogenous DNA). For example, a DNA molecule containing a non-host DNA segment encoding a polypeptide operably linked to a host DNA segment comprising a promoter is considered to be a heterologous DNA molecule. Conversely, a heterologous DNA molecule can comprise an endogenous structural gene operably linked with an exogenous promoter. A peptide or polypeptide encoded by a non-host DNA molecule is a "heterologous" peptide or polypeptide.

The term "selectable marker" denotes a nucleic acid that allows cells carrying this nucleic acid to be specifically selected for or against, in the presence of a corresponding "selection agent". A useful positive selectable marker is e.g. an antibiotic resistance gene. The selectable marker allows a cell which is transformed therewith to be selected for in the presence of the corresponding selection agent; a non-transformed cell is not capable to grow or survive under selective culture conditions, i.e. in the presence of the selection agent. Selectable markers can be positive, negative or bifunctional. Positive selectable markers allow the selection of cells carrying the marker, whereas negative selectable markers allow cells carrying the marker to be selectively eliminated. Typically, a selectable marker will confer resistance to a drug or compensate for a metabolic or catabolic defect in the cell. Selectable markers useful with eukaryotic cells include, e.g., the genes for aminoglycoside phosphotransferase (APH), such as the hygromycin phosphotransferase (HYG), neomycin and G418 APH, dihydrofolate reductase (DHFR), thymidine kinase (TK), glutamine synthetase (GS), asparagine synthetase, tryptophan synthetase (selection agent indole), histidinol dehydrogenase (selection agent histidinol D), and genes providing resistance to puromycin, bleomycin, phleomycin, chloramphenicol, Zeocin, and mycophenolic acid. Further selectable markers are reported in WO 92/08796 and WO 94/28143.

The term "expression machinery" as used within the current invention denotes the sum of the enzymes, cofactors, etc. of a cell, which are involved in the process beginning with the transcription of a nucleic acid or gene (i.e. also called "gene expression machinery") to the post-translational modification of the polypeptide encoded by the nucleic acid. The "expression machinery" e.g. comprises the steps of transcription of DNA into pre-mRNA, pre-mRNA splicing to mature mRNA, translation of the mRNA into a polypeptide, and post translational modification of the polypeptide.

The term "under conditions suitable for the expression of a heterologous polypeptide" denotes conditions which are used for the cultivation of a mammalian cell expressing a heterologous polypeptide and which are known to or can easily be determined by a person skilled in the art. It is also known to a person skilled in the art that these conditions may vary depending on the type of mammalian cell cultivated and type of protein expressed. In general the mammalian cell is cultivated at a temperature, e.g. between 20° C. and 40° C., for a period of time sufficient to allow effective protein production, e.g. for 4 to 28 days, in a volume of from 0.1 liter to $10^7$ liter.

The term "under conditions suitable for the growth of the non-transfected cell" denotes conditions which are generally used for the cultivation of a non-transfected cell of the same cell line. These conditions are known or can easily be determined by a person skilled in the art.

The term "recovering of the heterologous polypeptide" as used within the current application denotes precipitation, salting out, ultrafiltration, diafiltration, lyophilization, solvent volume reduction to obtain a concentrated solution, or chromatography. Generally chromatographic processes are used for the separation and purification of polypeptides. Different methods are well established and widespread used for protein recovery and purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

The term "immunoglobulin" refers to a protein consisting of one or more polypeptide(s) substantially encoded by immunoglobulin genes. The recognized immunoglobulin genes include the different constant region genes as well as the myriad immunoglobulin variable region genes. Immunoglobulins may exist in a variety of formats, including, for example, Fv, Fab, and F(ab)2 as well as single chains (scFv) or diabodies (e.g. Huston, J. S., et al., Proc. Natl. Acad. Sci. USA 85 (1988) 5879-5883; Bird, R. E., et al., Science 242 (1988) 423-426; in general, Hood, et al., Immunology, Benjamin N.Y., 2nd edition (1984); and Hunkapiller, T. and Hood, L., Nature 323 (1986) 15-16).

An immunoglobulin in general comprises two so called light chain polypeptides (light chain) and two so called heavy chain polypeptides (heavy chain). Each of the heavy and light chain polypeptides contains a variable domain (variable region) (generally the amino terminal portion of the polypeptide chain) comprising binding regions that are able to interact with an antigen. Each of the heavy and light chain polypeptides comprises a constant region (generally the carboxyl terminal portion). The constant region of the heavy chain mediates the binding of the antibody i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (Clq). The variable domain of an immunoglobulin's light or heavy chain in turn comprises different segments, i.e. four framework regions (FR) and three hypervariable regions (CDR).

An "immunoglobulin fragment" denotes a polypeptide comprising at least one domain of the group of domains comprising the variable domain, the $C_H1$ domain, the hinge-region, the $C_H2$ domain, the $C_H3$ domain, the $C_H4$ domain of a heavy chain of an immunoglobulin or the variable domain or the $C_L$ domain of a light chain of an immunoglobulin. Also comprised are derivatives and variants thereof. Additionally a variable domain, in which one or more amino acids or amino acid regions are deleted, may be present.

An "immunoglobulin conjugate" denotes a polypeptide comprising at least one domain of an immunoglobulin heavy or light chain conjugated via a peptide bond to a further polypeptide. The further polypeptide is a non-immunoglobulin peptide, such as a hormone, growth receptor, antifusogenic peptide or the like.

The current invention reports a promoter with a nucleotide sequence of SEQ ID NO: 02, or SEQ ID NO: 03, or SEQ ID NO: 04, or SEQ ID NO: 06

A method for the identification of a potential high producer cell clone is the linking of the expression of a selectable marker gene and a structural gene encoding a heterologous polypeptide via an internal ribosome entry site (IRES). With this design the expression of the heterologous polypeptide can be correlated with the expression of the selectable marker. Another method is gene amplification. Therein cells deficient of the enzyme dihydrofolate reductase (DHFR) are transfected with a vector/plasmid which contains a first expression cassette for the expression of the DHFR protein and a second expression cassette for the expression of a heterologous polypeptide. By using a culture medium depleted of glycine, hypoxanthine and thymidine selective culture conditions are established. For amplification a DHFR inhibitor, methotrexate (MTX), is added (Kaufman, R. J., et al., J Mol. Biol. 159 (1982) 601-621; U.S. Pat. No. 4,656,134). Generally may be used any kind of gene whose expression product is located/can be detected on the cell surface as a marker for enrichment and selection of transfectants. dLNGFR, a truncated form of the low-affinity nerve growth factor receptor, and thus inactive for signal transduction, which is expressed on the cell surface, and has proven to be a highly useful marker for cell biological analysis (Philipps, K., et al., Nat. Med. 2 (1996) 1154-1156 and Machl, A. W., et al., Cytometry 29 (1997) 371-374).

In order not to unnecessarily reduce the production of a heterologous polypeptide of interest the expression of the selectable marker, which is required for the selection of cells producing the heterologous polypeptide, i.e. of successfully transfected cells, should be as low as possible but nonetheless still detectable.

It has now surprisingly been found that this need can be fulfilled with a promoter according to the invention. By employing a promoter according to the current invention cells can be selected which express a heterologous polypeptide at a higher level compared to cells selected under the same conditions and not employing a promoter according to the current invention. It has surprisingly been found that with a promoter according to the invention a cell expressing a heterologous polypeptide can be isolated with reduced expenditure. Additionally it has been found that by employing a promoter according to the current invention cells can be selected that express a heterologous polypeptide at a higher level compared to cells selected by employing a full length SV40 promoter under the same conditions and selection agent concentrations.

The term "5' shortened SV40 promoter" as used within the current application denotes a wild-type SV40 promoter in which a defined number of consecutive nucleotides at the 5' end of the nucleic acid sequence have been deleted.

Thus, the current invention reports a promoter having, i.e. with, the nucleic acid sequence of SEQ ID NO: 02. SEQ ID NO: 02 comprises nucleotides 61 to 348 of the wild-type SV40 promoter of SEQ ID NO: 05, i.e. nucleotides 1 to 60 have been deleted. The preparation of the promoter with SEQ ID NO: 02 is shown in Example 1.

The current invention also reports a promoter having, i.e. with, the nucleic acid sequence of SEQ ID NO: 03. SEQ ID NO: 03 corresponds to nucleotides 130 to 348 of the wild-type SV40 promoter of SEQ ID NO: 05, i.e. nucleotides 1 to 129 have been deleted. The preparation of the promoter with SEQ ID NO: 03 is shown in Example 2.

The current invention finally reports a promoter having, i.e. with, the nucleic acid sequence of SEQ ID NO: 04. SEQ ID NO: 04 is nucleotides 177 to 348 of the wild-type SV40 promoter of SEQ ID NO: 05, i.e. nucleotides 1 to 176 have been deleted. The preparation of the promoter with SEQ ID NO: 04 is shown in Example 3.

The current invention finally reports a promoter having, i.e. with, the nucleic acid sequence of SEQ ID NO: 06. SEQ ID NO: 06 consists of nucleotides 203 to 348 of the wild-type SV40 promoter of SEQ ID NO: 05, i.e. nucleotides 1 to 202 have been deleted.

To determine the promoter strength of the promoters with a nucleic acid sequence of SEQ ID NO: 02 to 04 and 06 expression plasmids have been generated in which each of the different promoters is operably linked to a nucleic acid encoding GFP (green fluorescent protein, SEQ ID NO: 07). As can be seen from FIGS. 7 *a*) to *c*) the 5' deletion of nucleotides in the wild-type SV40 promoter nucleic acid reduces the promoter strength. The promoter of SEQ ID NO: 02 has approximately the same strength as the full-length wild-type SV40 promoter. The promoters of SEQ ID NO: 03 and 04 have promoter strength of approximately 56% and approximately 19%, respectively. Thus with the promoters according to the current invention the expression of a nucleic acid operably linked thereto can be reduced or limited compared to the wild-type SV40 promoter.

In simian virus 40 is the SV40 promoter preceded by two 72 bp repeats. In one embodiment of the current invention is the first 72 bp repeat deleted and the second 72 bp repeat maintained. In one embodiment the nucleic acid according to the invention comprises the nucleic acid of SEQ ID NO: 14 prior to the nucleic acid of SEQ ID NO: 04. In another embodiment the nucleic acid according to the invention comprises the second 72 bp repeat of SEQ ID NO: 14 of the simian virus 40 promoter. In a further embodiment in the nucleic acid according to the invention the first 72 bp repeat of the SV40 promoter is deleted and the second 72 bp repeat of the SV40 promoter is maintained. This is useful for the expression of a heterologous polypeptide. In this embodiment is the promoter according to the current invention, which is only containing the second 72 bp repeat of the wild type SV40 promoter, operably linked to a nucleic acid encoding a selectable marker. With the reduced promoter strength of this promoter the expression of the selectable marker is reduced whereas the expression of the heterologous polypeptide is maintained by using e.g. the wild type SV40 promoter of SEQ ID NO: 05. Thus, it has been found that the combination of a promoter according to the invention operably linked to a nucleic acid encoding a selectable marker and of a wild-type promoter, e.g. SV40 or CMV, operably linked to a nucleic acid encoding a heterologous polypeptide of interest results in an improved expression of the heterologous polypeptide compared to constructs in which the nucleic acid encoding a selectable marker as well as the nucleic acid encoding the heterologous polypeptide of interest are both operably linked to a wild-type promoter.

In stable cell clones the nucleic acid encoding the selectable marker and the nucleic acid encoding the heterologous polypeptide as well as their corresponding promoters are integrated jointly in the genome of said cell. As the location of the integration in the genome is a random process a selection step is normally carried out. In this selection step only cells are selected in which the joint nucleic acids are incorporated in the genome is close proximity of a transcriptionally highly active locus. Cells either having incorporated the nucleic acid afar from such a locus or having incorporated both nucleic acids at different loci are eliminated by the selection step.

Another aspect of the current invention is a nucleic acid consisting of a nucleic acid sequence of SEQ ID NO: 02, or SEQ ID NO: 03, or SEQ ID NO: 04, or SEQ ID NO: 06, which has a promoter strength of 90% or more, or 40% to less than 90%, or less than 40% of the promoter strength of the wild-type SV40 promoter of SEQ ID NO: 05 when operably linked to the nucleic acid of SEQ ID NO: 07.

In a preferred embodiment has the nucleic acid the nucleic acid sequence of SEQ ID NO: 04 and a promoter strength of 20% or less of the promoter strength of the wild-type SV40 promoter of SEQ ID NO: 05 when each of them individually is operably linked to the nucleic acid of SEQ ID NO: 07.

As the nucleic acid and the promoter, respectively, according to the invention each has reduced promoter strength, i.e. a nucleic acid operably linked thereto is transcribed at a reduced amount or with a reduced rate when compared to the wild-type SV40 promoter, they are useful in multiple applications.

For example, they can be used to promote the expression of an operably linked selection marker allowing for the selection of a cell carrying this selection marker without requiring a large fraction of the capacity of the cell's protein expression machinery. Thereby the expression of an e.g. co-expressed heterologous polypeptide is not negatively affected.

Another aspect of the current invention is a method for the selection of a cell expressing a heterologous polypeptide comprising the steps of
a) transfecting a eukaryotic cell with a nucleic acid comprising
   i) a first expression cassette comprising a nucleic acid encoding a heterologous polypeptide,
   ii) a second expression cassette comprising a first nucleic acid of SEQ ID NO: 04 and a second nucleic acid encoding a selectable marker, whereby the first nucleic acid is operably linked to the second nucleic acid,
b) cultivating said transfected cell under conditions suitable for growth of the non-transfected eukaryotic cell,
c) selecting a cell propagating in step b) and also
   i) propagating under selection condition, or
   ii) expressing the selectable marker.

Cells suitable in this method are e.g. CHO cells, BHK cells, PER.C6® cells, HEK cells, HeLa cells, SP2/0 cells, NS0 cells, myeloma cells, or hybridoma cells. In one embodiment the cell is a mammalian cell, in a preferred embodiment the cell is selected from a CHO cell, BHK cell, HEK cell, Sp2/0 cell, or a PER.C6® cell.

The heterologous polypeptide may be any heterologous polypeptide of interest, such as e.g. prodrugs, enzymes, enzyme fragments, enzyme inhibitors, enzyme activators, biologically active polypeptides, hedgehog proteins, bone morphogenetic proteins, growth factors, erythropoietin, thrombopoietin, G-CSF, interleukins, interferons, immunoglobulins, or antifusogenic peptides, or fragments thereof, or conjugates thereof. In one embodiment the heterologous polypeptide is an immunoglobulin, or an immunoglobulin fragment, or an immunoglobulin conjugate.

In one embodiment step c) of the method is selecting a cell propagating in step b) under selective culture conditions, i.e. in the presence of a selection agent. In another embodiment step c) of the method is selecting a cell propagating in step b) and expressing the selectable marker encoded by said second nucleic acid. In the first embodiment is the transfected cell cultivated in the presence of a selection agent that inhibits the propagation of cells not transfected or not sufficiently expressing the second nucleic acid encoding the selectable marker. In the second embodiment is the transfected cell cultivated in the absence of a selection agent and selection is by the detection of the expression of the selectable marker, e.g. by FACS or sight inspection.

Selection of cells can be performed in a single step or in multiple steps. In a single/multiple step procedure the first selection can be performed based e.g. on a threshold level of a selectable marker, such as e.g. dLNGFR or GFP. For example, for selection by flow cytometry (e.g. by FACS—Fluorescence Activated Cell Sorting) a fluorescence threshold level is set and cells with a fluorescence above this threshold level are selected. Alternatively cells within the top 1-15% (i.e. the 15% of the cells with the most intense detectable label), or top 1-10%, or top 1-5%, or top 5-10% of fluorescence intensity of the sample population can be collected. An alternative method for the selection of a cell is immunological binding, e.g. to magnetic beads coated with Protein A or specific immunoglobulins. The selected panel of cells may be taken as basic population for a further selection step, e.g. by single cell seeding, cultivation and ELISA analysis (Enzyme-linked Immunosorbent Assay), or by limited dilution cloning, or by expanding by cultivation for several days and a further FACS selection, or by a further FACS selection with a higher threshold level, which can for example be based on the fluorescence intensities detected in a preceding FACS selection, or by an immunoprecipitation method (see e.g. WO 2005/020924). Selecting a cell according to the invention can in one embodiment be performed by a method selected from flow cytometry, ELISA, immunoprecipitation, immunoaffinity column chromatography, magnetic bead immunoaffinity sorting, microscopy-based isolation methods, or immunological binding. In another embodiment selecting a cell according to the invention can be performed by a method selected from flow cytometry, ELISA, immunoprecipitation, immunoaffinity column chromatography, magnetic bead immunoaffinity sorting, microscopy-based isolation methods, or immunological binding, followed by a method selected from single cell seeding and cultivation, limited dilution, or expanding by cultivation, followed by a method selected from FACS, immunoprecipitation, immunoaffinity column chromatography, magnetic bead immunoaffinity sorting, microscopy-based isolation methods, or ELISA.

The final aspect of the current invention is a method for the expression of a heterologous polypeptide in a cell by operably linking a promoter according to the invention to a nucleic acid encoding said heterologous polypeptide. This method is suitable for the expression e.g. of large proteins with low solubilities or slow folding kinetics. The reduction of the amount or rate of expression of a heterologous polypeptide or of the transcription of a nucleic acid is advisable if the heterologous polypeptide or nucleic acid adversely affects the host cell or reduces the overall production yield of functionable, i.e. correctly folded, heterologous polypeptide. Therefore, one aspect of the current invention is the expression or production of a heterologous polypeptide with reduced fraction of not functionable, i.e. not correctly folded, polypeptide. If the heterologous polypeptide expressed in the host cell e.g. exceeds a certain size with respect to weight, or amino acid number, or number of subunits, or number of secondary modifications, it probably will be obtained after the cultivation of the host cell in a non-functionable, i.e. non-active or not correctly folded, form. One possibility to circumvent this problem is to reduce the amount, i.e. the rate, of the protein expression. As protein expression is regulated by the strength of the operably linked promoter, the promoters according to the invention are well suited therefore.

Therefore, the current invention comprises a method for the expression or production of a heterologous polypeptide with reduced fraction of not functionable polypeptide wherein the method comprises the following steps in this order:
a) transfecting a mammalian cell with a nucleic acid comprising an expression cassette comprising a promoter of SEQ ID NO: 02, or SEQ ID NO: 03, or SEQ ID NO: 04, or SEQ ID NO: 06 operably linked to a nucleic acid encoding a heterologous polypeptide,
b) selecting a cell transfected in step a),
c) cultivating the selected cell under conditions suitable for the expression of the heterologous polypeptide,
d) recovering the heterologous polypeptide from the cell or the cultivation medium.

In one embodiment of this aspect of the current invention the mammalian cell is a CHO cell, a BHK cell, a HEK cell, a Sp2/0 cell, or a PER.C6® cell. In one embodiment of this method the promoter is of SEQ ID NO: 03 or SEQ ID NO: 04. In another embodiment has the promoter the SEQ ID NO: 04. In a further embodiment is the nucleic acid encoding a heterologous polypeptide encoding an immunoglobulin, or an immunoglobulin-fragment, or an immunoglobulin-conjugate. In still another embodiment comprises the nucleic acid a second expression cassette encoding a selectable marker.

The following examples, sequence listing and figures are provided to aid the understanding of the present invention, the true scope of which is set forth in the appended claims. It is understood that modifications can be made in the procedures set forth without departing from the spirit of the invention.

EXAMPLE 1

Figure 1:
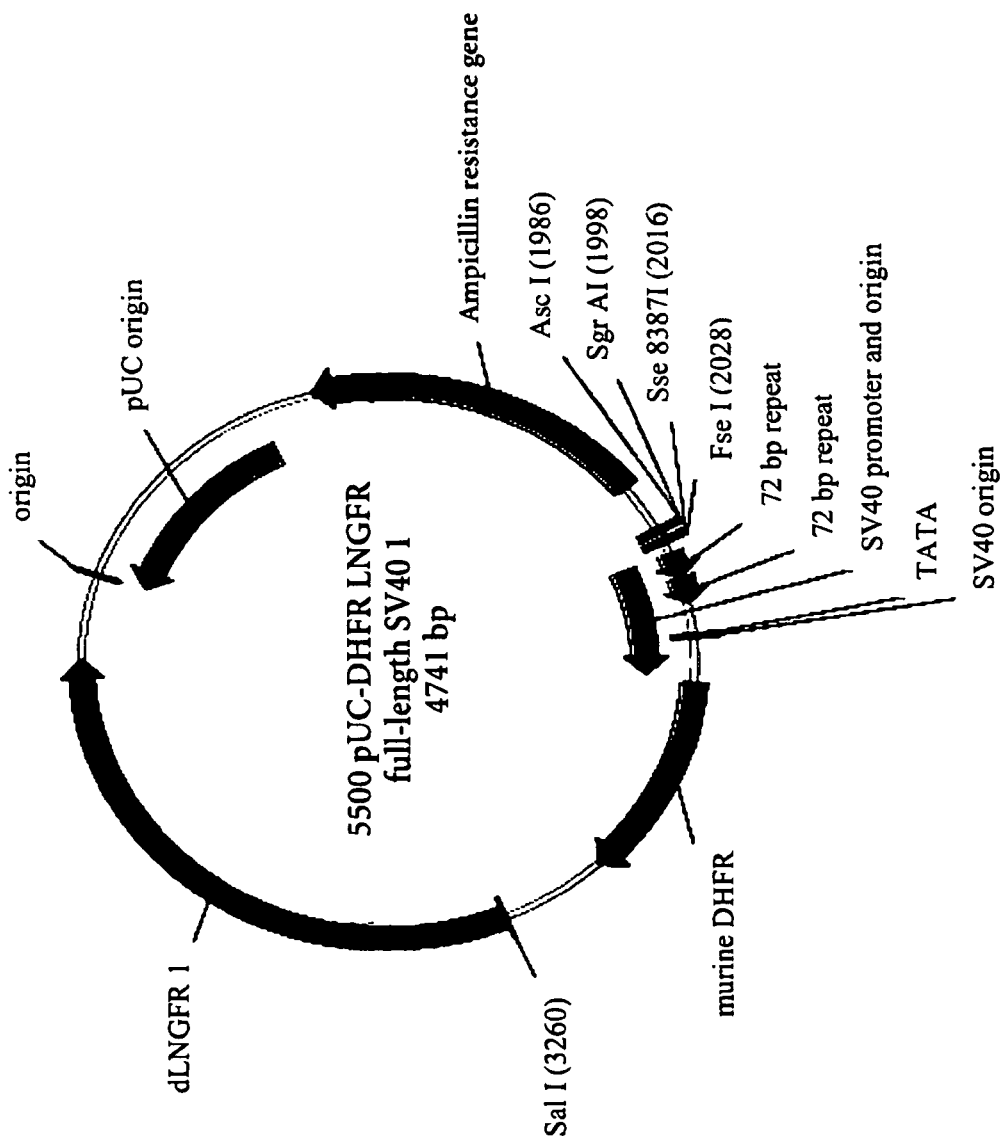
FIG. 1 Plasmid map of plasmid 5500.

Construction of Nucleic Acid of SEQ ID NO: 02

The 5' shortened SV40 promoter of SEQ ID NO: 02 was obtained via a PCR reaction with the full length SV40 promoter as template operably linked to a nucleic acid encoding dLNGFR (plasmid 4788). The PCR mixture was: 1×PWO buffer (Roche Molecular Biochemicals, Mannheim, Germany) supplemented with 2 mM MgSO$_4$, 200 µM dNTPs PCR Nucleotide Mix (Roche Molecular Biochemicals, Mannheim, Germany), 1 µM forward primer of SEQ ID NO: 08, 1 µM reverse primer of SEQ ID NO: 13, 50 ng template-DNA of plasmid 4788, 2.5 U PWO-DNA polymerase (PWO=*Pyrococcus woesei*; Roche Molecular Biochemicals, Mannheim, Germany), ad 100 µL with doubly distilled ultrapure water. The PCR conditions were: 1 min at 94° C., 1 cycle; 0.5 min at 94° C., 25 cycles; 0.5 min at 55° C., 25 cycles; 1 min at 72° C., 25 cycles; 5 min at 72° C., 1 cycle.

EXAMPLE 2

Construction of Nucleic Acid of SEQ ID NO: 03

The 5' shortened SV40 promoter variant of SEQ ID NO: 03 was obtained via a PCR reaction with the full length SV40 promoter as template operably linked to a nucleic acid encoding dLNGFR from plasmid 4788. The PCR mixture was: 1×PWO buffer supplemented with 2 mM MgSO$_4$, 200 µM dNTPs PCR Nucleotide Mix, 1 µM forward primer of SEQ ID NO: 09, 1 µM reverse primer of SEQ ID NO: 13, 50 ng template-DNA of plasmid 4788, 2.5 U PWO-DNA polymerase, ad 100 µL with doubly distilled ultrapure water. The PCR conditions were: 1 min at 94° C., 1 cycle; 0.5 min at 94° C., 25 cycles; 0.5 min at 55° C., 25 cycles; 1 min at 72° C., 25 cycles; 5 min at 72° C., 1 cycle.

EXAMPLE 3

Construction of Nucleic Acid of SEQ ID NO: 04

The 5' shortened SV40 promoter variant of SEQ ID NO: 04 was obtained via a PCR reaction with the full length SV40 promoter as template operably linked to a nucleic acid encoding dLNGFR (plasmid 4788). The PCR mixture was: 1×PWO buffer supplemented with 2 mM MgSO$_4$, 200 µM dNTPs PCR Nucleotide Mix, 1 µM forward primer of SEQ ID NO: 10, 1 µM reverse primer of SEQ ID NO: 13, 50 ng template-DNA of plasmid 4788, 2.5 U PWO-DNA polymerase, ad 100 µL, with doubly distilled ultrapure water. The PCR conditions were: 1 min at 94° C., 1 cycle; 0.5 min at 94° C., 25 cycles; 0.5 min at 55° C., 25 cycles; 1 min at 72° C., 25 cycles; 5 min at 72° C., 1 cycle.

EXAMPLE 4

Construction of Further Promoters

Further 5' shortened SV40 promoter variants were produced via a PCR reaction with the full length SV40 promoter as template operably linked to a nucleic acid encoding dLNGFR. The PCR mixture was: 1×PWO buffer supplemented with 2 mM MgSO$_4$, 200 µM dNTPs PCR Nucleotide Mix, 1 µM forward primer of SEQ ID NO: 11 (yielding SEQ ID NO: 06) or SEQ ID NO: 12, 1 µM reverse primer of SEQ ID NO: 13, 50 ng template-DNA of Plasmid 4788, 2.5 U PWO-DNA polymerase, ad 100 µL with bidistilled ultrapure water. The PCR conditions were: 1 min at 94° C., 1 cycle; 0.5 min at 94° C., 25 cycles; 0.5 min at 55° C., 25 cycles; 1 min at 72° C., 25 cycles; 5 min at 72° C., 1 cycle.

EXAMPLE 5

Expression of dLNGFR Operably Linked to SEQ ID NO: 02, 03, 04, and 06

Figure 2:
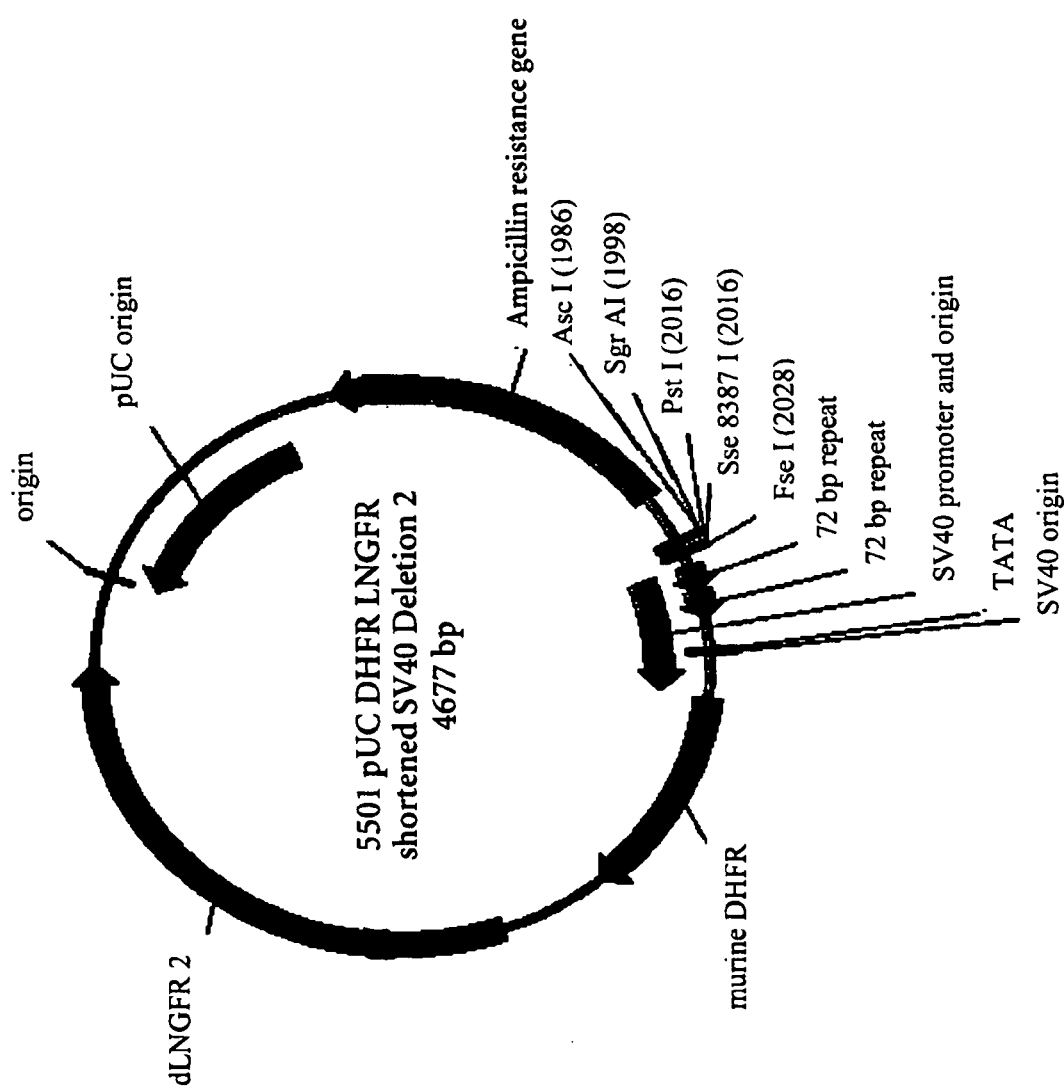
FIG. 2 Plasmid map of plasmid 5501.

The primer with which the nucleic acids of SEQ ID NO: 02, 03, 04, and 06 were obtained contained restriction sites of the restriction endonucleases SalI and EcoRI. Using these restriction sites/restriction endonucleases these nucleic acids operably linked to a nucleic acid encoding dLNGFR (for LNGFR (low affinity nerve growth factor) see e.g. Philipps, K., et al., Nat. Med. 2 (1996) 1154-1156; or Machl, A. W., et al., Cytometry 29 (1997) 371-374) have been ligated into the plasmid 4736-pUC-DHFR, which has been linearized using the restriction sites SalI and PvuII. The resulting plasmids are:

5500-pUC-DHFR_dLNGFR_wildtypeSV40 (plasmid map in FIG. 1), 5501-pUC-DHFR_dLNGFR_Shortening_2 (plasmid map in FIG. 2), 5502-pUC-DHFR_dLNGFR_Shortening_3, 5503-pUC-DHFR_dLNGFR_Shortening_4, 5504-pUC-DHFR_dLNGFR_Shortening_6.

HEK 293 EBNA cells have been transfected with these plasmids and the encoded polypeptide was transiently expressed. After 48 h the expression of dLNGFR has been verified via FACS. For the determination of the promoter strength (expression strength) of the different promoters the expressed surface marker dLNGFR was fluorescence marked via an anti-dLNGFR antibody.

Figure 6:
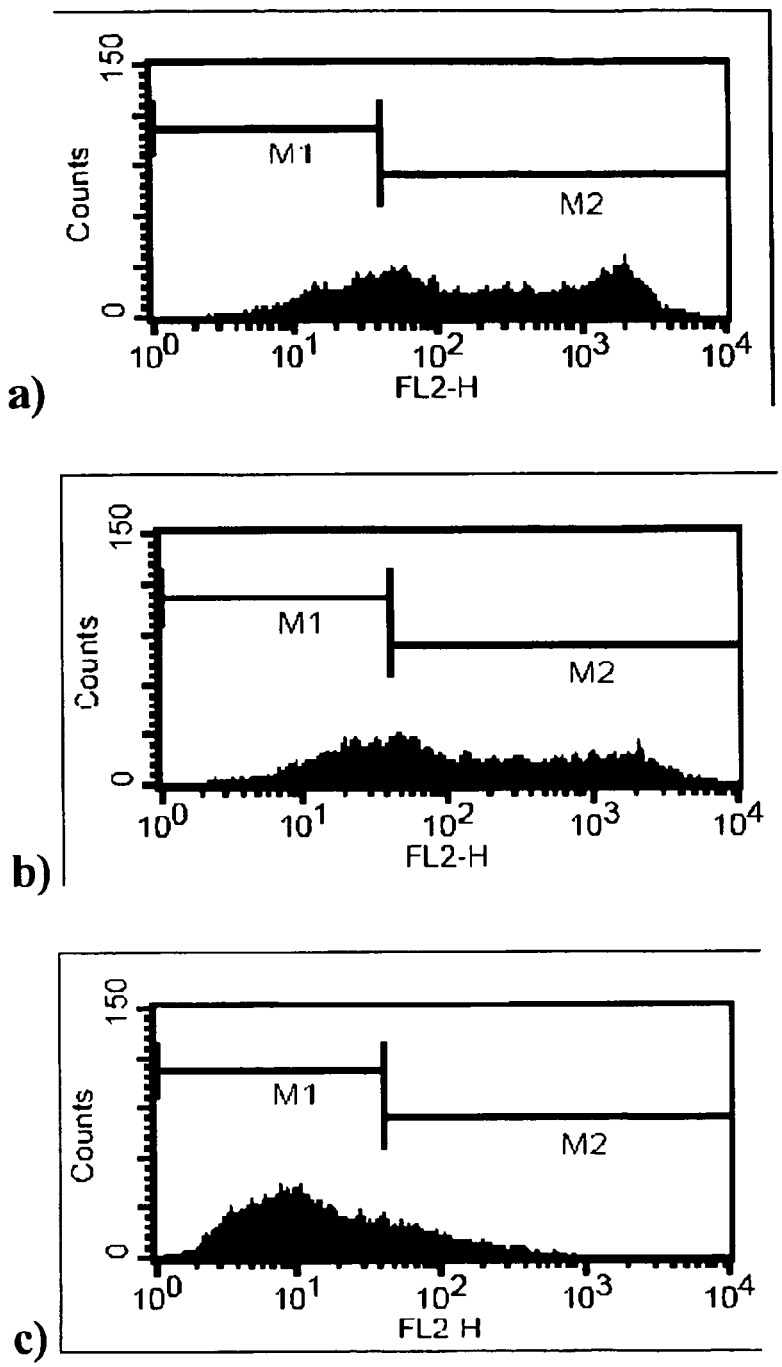
FIG. 6 FACS analysis of dLNGFR-expression of HEK293EBNA-cells transfected with
  a) an expression cassette of SEQ ID NO: 05 operably linked to SEQ ID NO: 07,
  b) an expression cassette of SEQ ID NO: 04 operably linked to SEQ ID NO: 07,
  c) an expression cassette of SEQ ID NO: 06 operably linked to SEQ ID NO: 07.

For each determination approximately $0.5 \times 10^6$ to $1.0 \times 10^6$ cells have been detached by the addition of 1 ml Accutase® per 6 wells (GIBCO Invitrogen, Karlsruhe, Germany). The detached cells were transferred in a vial and washed once with RPMI 1640 medium supplemented with 10% (v/v) fetal bovine serum. Afterwards the cells were precipitated by centrifugation (1,500 rpm, 5 min.) and the supernatant was discarded. All following steps were performed at 0 to 2° C. on or in an ice bath. The cell pellet was resuspended in 100 µl of a solution containing the anti-dLNGFR antibody at 30 µg/ml. After an incubation period of 30 minutes the samples were diluted by the addition of 2 ml of ice-cold RPMI 1640 medium with subsequent precipitation by centrifugation. The pellet was resuspended in 100 µL of a secondary antibody solution, a goat anti-mouse-IgG antibody conjugated to Phycoerythrin (Caltag Laboratories, Burlingame, Calif., USA), at a concentration of 20 µg/ml. The sample was incubated in the dark for 30 min. on ice. After a washing and centrifugation step the sample was resuspended in 500 µl medium and stored in the dark on ice until the measurement. The FACS analysis was evaluated using the FACSCalibur software (Cell Quest Pro). The results are shown in FIG. 6.

Results of the FACS analysis:

5500-pUC-DHFR_dLNGFR_wildtypeSV40 (FIG. 6a):

| Marker | Left, Right | Events | % Gated | % Total | Mean | Median |
|---|---|---|---|---|---|---|
| All | 1, 9910 | 8067 | 100.00 | 80.67 | 567.61 | 128.64 |
| M1 | 1, 40 | 2134 | 26.45 | 21.34 | 21.84 | 21.29 |
| M2 | 40, 9910 | 5956 | 73.83 | 59.56 | 761.11 | 345.99 |

5501-pUC-DHFR_dLNGFR_Shortening_2:

| Marker | Left, Right | Events | % Gated | % Total | Mean | Median |
|---|---|---|---|---|---|---|
| All | 1, 9910 | 7377 | 100.00 | 73.77 | 564.33 | 168.49 |
| M1 | 1, 40 | 1365 | 18.50 | 13.65 | 24.69 | 25.48 |
| M2 | 40, 9910 | 6027 | 81.70 | 60.27 | 685.24 | 291.64 |

5502-pUC-DHFR_dLNGFR_Shortening_3:

| Marker | Left, Right | Events | % Gated | % Total | Mean | Median |
|---|---|---|---|---|---|---|
| All | 1, 9910 | 7643 | 100.00 | 76.43 | 582.85 | 129.80 |
| M1 | 1, 40 | 1959 | 25.63 | 19.59 | 22.68 | 22.88 |
| M2 | 40, 9910 | 5708 | 74.68 | 57.08 | 772.82 | 339.82 |

5503-pUC-DHFR_dLNGFR_Shortening_4 (FIG. 6b):

| Marker | Left, Right | Events | % Gated | % Total | Mean | Median |
|---|---|---|---|---|---|---|
| All | 1, 9910 | 7440 | 100.00 | 74.40 | 436.61 | 69.78 |
| M1 | 1, 40 | 2603 | 34.99 | 26.03 | 20.87 | 19.99 |
| M2 | 40, 9910 | 4852 | 65.22 | 48.52 | 658.42 | 250.29 |

5504-pUC-DHFR_dLNGFR_Shortening_6 (FIG. 6c):

| Marker | Left, Right | Events | % Gated | % Total | Mean | Median |
|---|---|---|---|---|---|---|
| All | 1, 9910 | 8404 | 100.00 | 84.04 | 31.67 | 11.65 |
| M1 | 1, 40 | 6685 | 79.55 | 66.85 | 12.05 | 9.14 |
| M2 | 40, 9910 | 1732 | 20.61 | 17.32 | 107.45 | 74.32 |

It can be seen that the mean fluorescence intensity of the labeled dLNGFR expressed from plasmid 5504 shows a significant reduction of expression with about 85% reduction.

EXAMPLE 6

Expression of GFP Operably Linked to SEQ ID NO: 02, 03, 04, and 06

Figure 3:
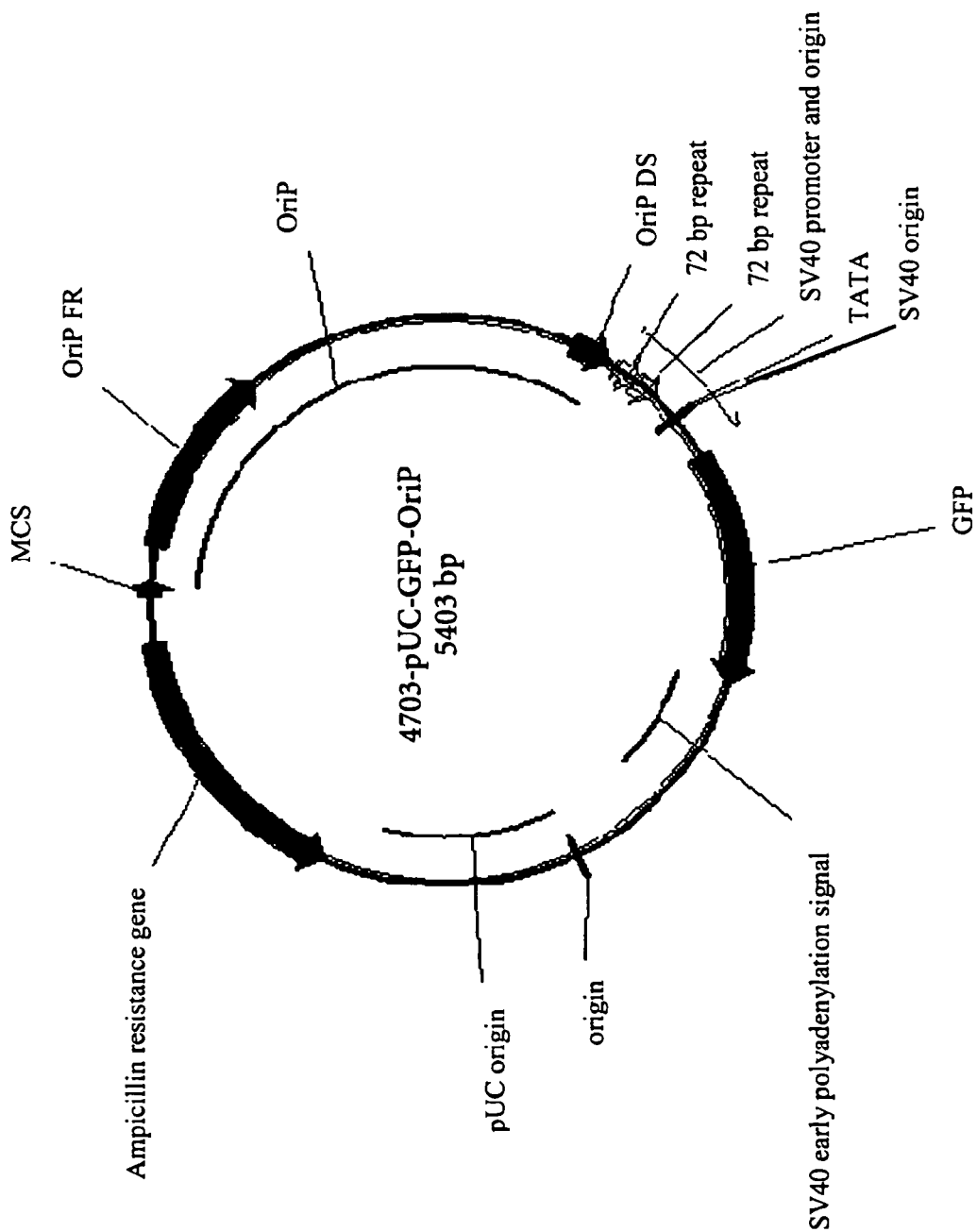
FIG. 3 Plasmid map of plasmid 4703.
Figure 4:
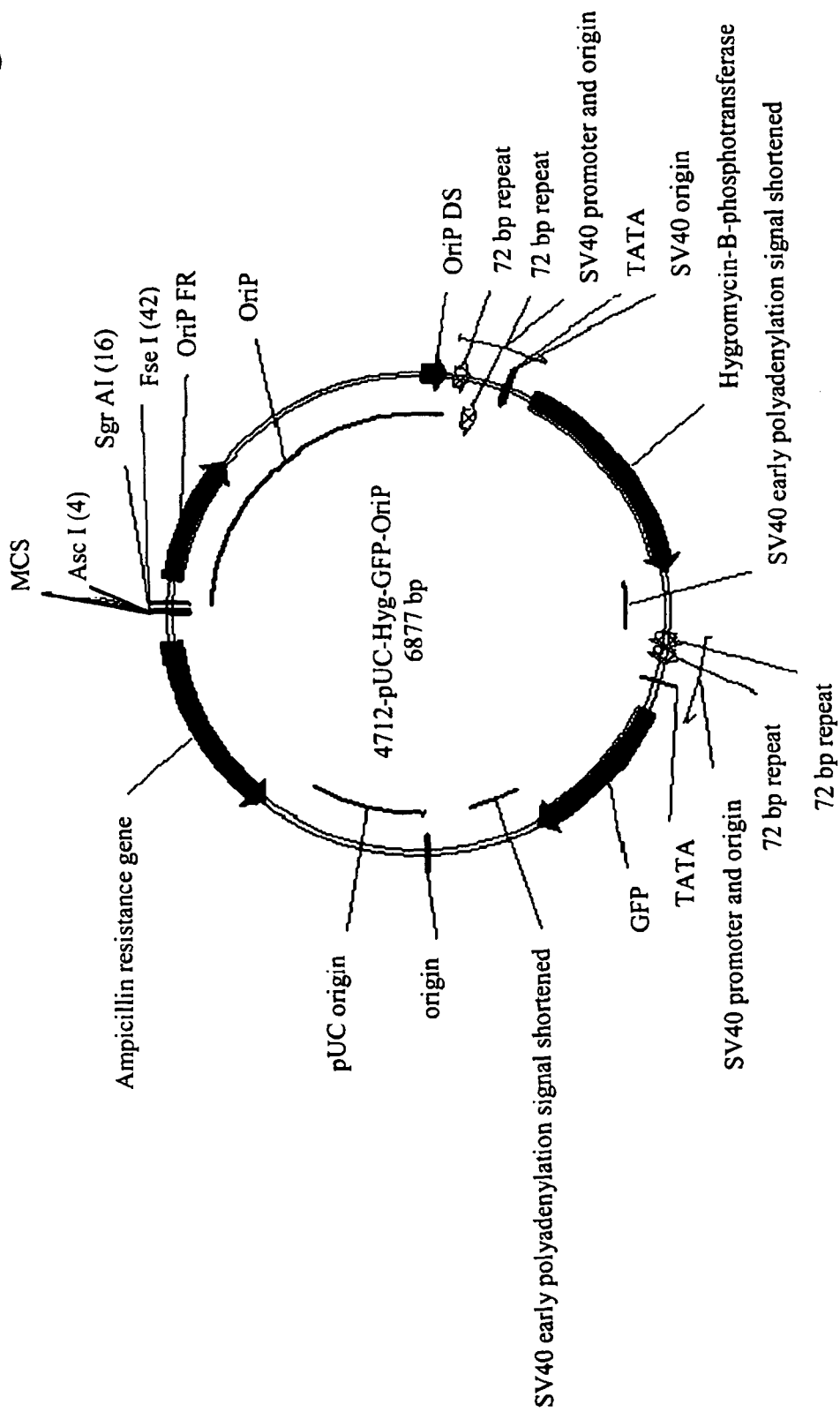
FIG. 4 Plasmid map of plasmid 4712.
Figure 5:
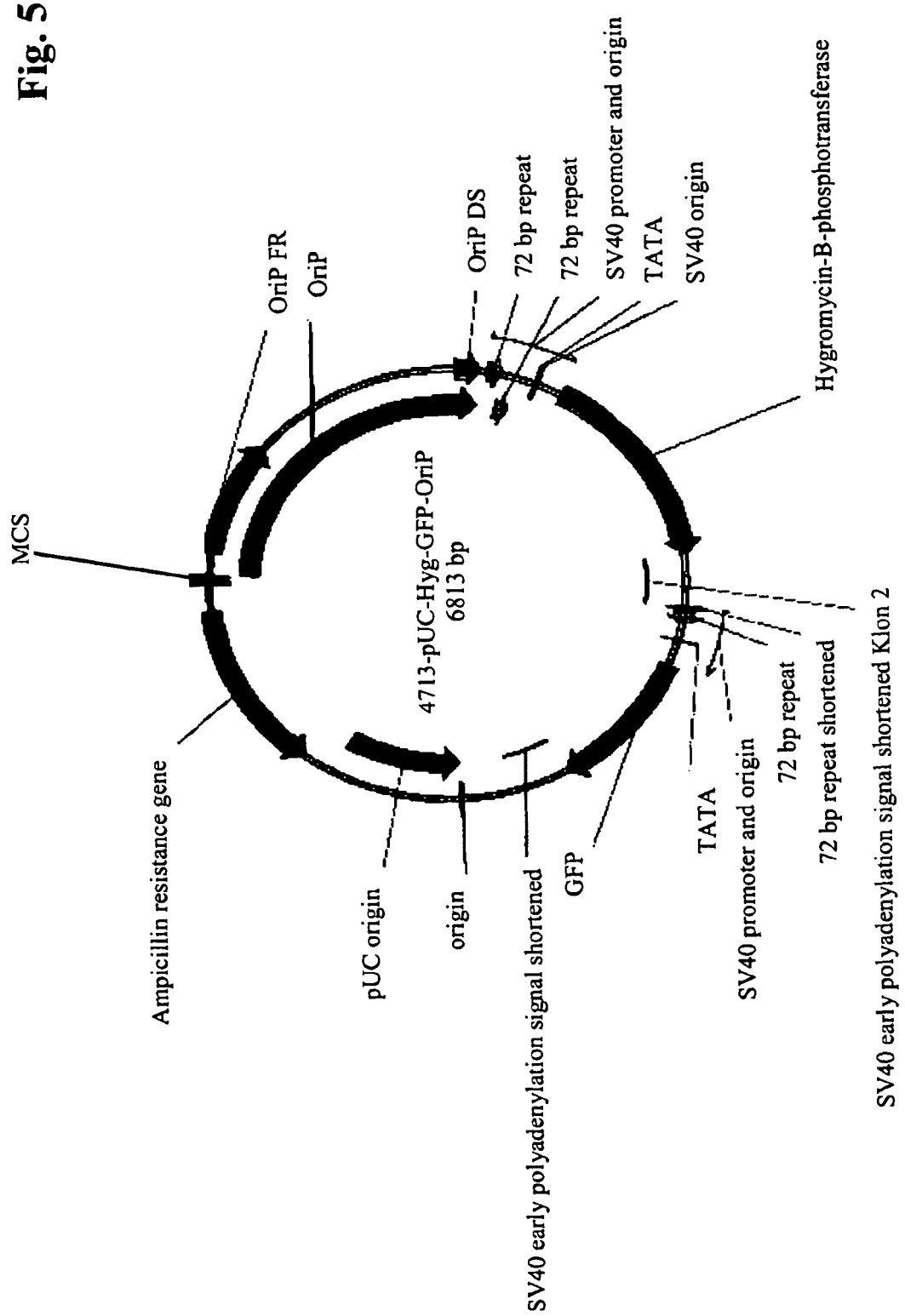
FIG. 5 Plasmid map of plasmid 4713.

The primer with which the nucleic acids of SEQ ID NO: 02, 03, 04, and 06 were obtained contained restriction sites of the restriction endonucleases SalI and EcoRI. Using these restriction sites/restriction endonucleases these nucleic acids operably linked to a nucleic acid encoding GFP (SEQ ID NO: 07) have been ligated into the plasmid 4703-pUC-OriP (FIG. 3), which has been linearized using the restriction sites SalI and PvuII. The resulting plasmids were:

4712-pUC-Hyg_GFP_wildtypeSV40 (plasmid map in FIG. 4), 4713-pUC-Hyg_GFP_Shortening_2 (plasmid map in FIG. 5), 4714-pUC-Hyg_GFP_Shortening_3, 4715-pUC-Hyg_GFP_Shortening_4, 4716-pUC-Hyg_GFP_Shortening_6.

Figure 7:
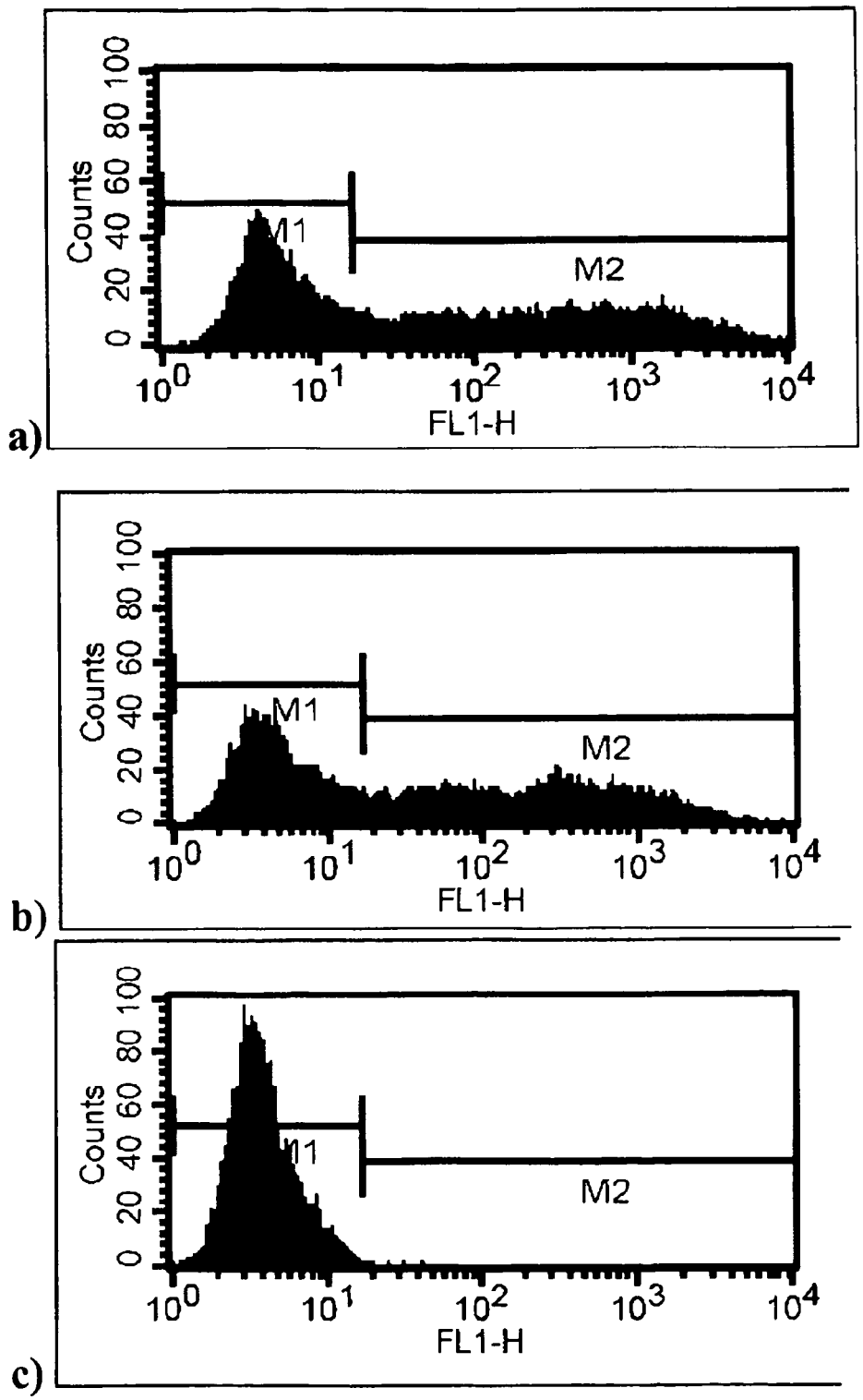
FIG. 7 FACS analysis of GFP-expression of HEK293EBNA-cells transfected with
  a) an expression cassette of SEQ ID NO: 05 operably linked to SEQ ID NO: 07,
  b) an expression cassette of SEQ ID NO: 03 operably linked to SEQ ID NO: 07,
  c) an expression cassette of SEQ ID NO: 06 operably linked to SEQ ID NO: 07.

For each determination approximately $5 \times 10^5$ to $1 \times 10^6$ cells have been detached by the addition of 1 ml Accutase® per 6 wells (GIBCO Invitrogen, Karlsruhe, Germany). The detached cells were transferred in a vial and resuspended in 3 ml RPMI 1640 medium supplemented with 10% (v/v) fetal bovine serum. Afterwards the cells were precipitated by centrifugation (1,500 rpm, 5 min.) and the supernatant was discarded. The cell pellet was resuspended in 500 µl medium. For the differentiation of living and dead cells 1 µl propidium iodide was added. The cells were resuspended shortly prior to the FACS measurement. The FACS analysis was evaluated using the FACSCalibur software (Cell Quest Pro). The results are shown in FIG. 7.

Results of the FACS Analysis:
4712-pUC-Hyg_GFP_wildtypeSV40 (FIG. 7a):

| Marker | Left, Right | Events | % Gated | % Total | Mean | Median |
|---|---|---|---|---|---|---|
| All | 1, 9910 | 8390 | 100.00 | 33.90 | 385.26 | 17.15 |
| M1 | 1, 16 | 4162 | 49.61 | 41.62 | 5.92 | 4.91 |
| M2 | 16, 9910 | 4240 | 50.54 | 42.40 | 756.58 | 302.32 |

4713-pUC-Hyg_GFP_Shortening_2:

| Marker | Left, Right | Events | % Gated | % Total | Mean | Median |
|---|---|---|---|---|---|---|
| All | 1, 9910 | 8576 | 100.00 | 85.76 | 514.24 | 45.73 |
| M1 | 1, 16 | 3635 | 42.39 | 36.35 | 5.72 | 4.61 |
| M2 | 16, 9910 | 4948 | 57.70 | 49.48 | 887.12 | 392.42 |

4714-pUC-Hyg_GFP_Shortening_3 (FIG. 7b):

| Marker | Left, Right | Events | % Gated | % Total | Mean | Median |
|---|---|---|---|---|---|---|
| All | 1, 9910 | 8538 | 100.00 | 85.38 | 215.22 | 15.96 |
| M1 | 1, 16 | 4289 | 50.23 | 42.89 | 5.44 | 4.26 |
| M2 | 16, 9910 | 4258 | 49.87 | 42.58 | 426.11 | 203.51 |

4715-pUC-Hyg_GFP_Shortening_4:

| Marker | Left, Right | Events | % Gated | % Total | Mean | Median |
|---|---|---|---|---|---|---|
| All | 1, 9910 | 8601 | 100.00 | 86.01 | 53.76 | 7.37 |
| M1 | 1, 16 | 5606 | 65.18 | 56.06 | 5.59 | 4.41 |
| M2 | 16, 9910 | 3012 | 35.02 | 30.12 | 143.20 | 73.65 |

4716-pUC-Hyg_GFP_Shortening_6 (FIG. 7c):

| Marker | Left, Right | Events | % Gated | % Total | Mean | Median |
|---|---|---|---|---|---|---|
| All | 1, 9910 | 7622 | 100.00 | 76.22 | 4.09 | 3.52 |
| M1 | 1, 16 | 7614 | 99.90 | 76.14 | 4.07 | 3.52 |
| M2 | 16, 9910 | 8 | 0.10 | 0.08 | 22.46 | 18.85 |

It can be seen that the mean fluorescence intensity of the GFP expressed from plasmid 4714 or plasmid 4715 shows a significant reduction of expression with about 50% and 75% reduction, respectively. With plasmid 4716 no detectable expression of GFP was found.

The invention claimed is:

1. A method for the selection of a cell expressing a heterologous polypeptide to the cell expressing it comprising the following steps:
   a) transfecting an isolated eukaryotic cell with a nucleic acid comprising
      i) a first expression cassette comprising a nucleic acid encoding a heterologous polypeptide,
      ii) a second expression cassette comprising a first nucleic acid comprising the sequence of SEQ ID NO: 04 and a second nucleic acid encoding a selectable marker selected from the group consisting of hygromycin phosphotransferase, neomycin and G418 aminoglycoside phosphotransferase, dLNGFR and GFP, whereby said first and second nucleic acid are operably linked,
   b) cultivating said transfected cell under conditions suitable for the growth of non-transfected cell; and
   c) cultivating said cells under selective culture conditions;
   d) selecting a cell propagating in step b) and under selective culture conditions in step c).

2. The method of claim 1, wherein step d) of said method is selecting a cell propagating in step b) and expressing the selectable marker encoded by said second nucleic acid.

3. A method for the expression of a heterologous polypeptide to the cell expressing it, comprising the following steps:
   a) transfecting an isolated eukaryotic cell with a nucleic acid comprising an expression cassette comprising a first nucleic acid having the sequence of SEQ ID NO: 04 operably linked to a second nucleic acid encoding a heterologous polypeptide,
   b) selecting a cell transfected in step a),
   c) cultivating the selected cell of step b) under conditions suitable for the expression of said heterologous polypeptide; and
   d) recovering the heterologous polypeptide from the cell or the cultivation medium.

4. The method of claim 3, wherein the nucleic acid comprises a second expression cassette encoding an aminoglycoside phosphotransferase selected from the group consisting of hygromycin phosphotransferase, neomycin and G418 aminoglycoside phosphotransferase.

5. The method of claim 1, wherein said eukaryotic cell is a mammalian cell.

6. The method of claim 5, wherein said mammalian cell is a CHO cell, a BHK cell, a HEK cell or, a Sp2/0 cell.

7. The method of claim 6, wherein said mammalian cell is a CHO cell or a HEK cell.

8. The method of claim 1, wherein said heterologous polypeptide is an immunoglobulin, or an immunoglobulin-fragment, or an immunoglobulin-conjugate.

9. The method of claim 3, wherein said first nucleic acid is a nucleic acid having the sequence of SEQ ID NO: 04 and has a promoter strength of 20% or less of the SV40 promoter of SEQ ID NO: 05 when operably linked to the nucleic acid of SEQ ID NO: 07.

* * * * *

```
                        SEQUENCE LISTING

<160> NUMBER OF SEQ ID NOS: 14

<210> SEQ ID NO 1
<211> LENGTH: 5243
<212> TYPE: DNA
<213> ORGANISM: Simian virus 40

<400> SEQUENCE: 1
gcctcggcct ctgcataaat aaaaaaaatt agtcagccat ggggcggaga atgggcggaa      60
ctgggcggag ttaggggcgg gatgggcgga gttaggggcg ggactatggt tgctgactaa     120
ttgagatgca tgctttgcat acttctgcct gctggggagc ctggggactt tccacacctg     180
gttgctgact aattgagatg catgctttgc atacttctgc ctgctgggga gcctggggac     240
tttccacacc ctaactgaca cacattccac agctggttct ttccgcctca gaaggtacct     300
aaccaagttc ctctttcaga ggttatttca ggccatggtg ctgcgccggc tgtcacgcca     360
ggcctccgtt aaggttcgta ggtcatggac tgaaagtaaa aaaacagctc aacgccttt     420 tgtgtttgtt ttagagcttt tgctgcaatt ttgtgaaggg gaagatactg ttgacggaa     480 acgcaaaaaa ccagaaaggt taactgaaaa accagaaagt taactggtaa gtttagtctt     540
tttgtctttt atttcaggtc catgggtgct gctttaacac tgttggggga cctaattgct     600
actgtgtctg aagctgctgc tgctactgga ttttcagtag ctgaaattgc tgctggagag     660
gccgctgctg caattgaagt gcaacttgca tctgttgcta ctgttgaagg cctaacaacc     720
tctgaggcaa ttgctgctat aggcctcact ccacaggcct atgctgtgat atctgggct     780 cctgctgcta tagctggatt tgcagcttta ctgcaaactg tgactggtgt gagcgctgtt     840
gctcaagtgg ggtatagatt ttttagtgac tgggatcaca aagtttctac tgttggttta     900
tatcaacaac caggaatggc tgtagatttg tataggccag atgattacta tgatatttta     960
tttcctggag tacaaaccct tgttcacagt gttcagtatc ttgaccccag acattgggt    1020 ccaacacttt ttaatgccat ttctcaagct ttttggcgtg taatacaaaa tgacattcct    1080
```

```
aggctcacct cacaggagct tgaaagaaga acccaaagat atttaaggga cagtttggca    1140 aggttttag aggaaactac ttggacagta attaatgctc ctgttaattg gtataactct    1200
ttacaagatt actactctac tttgtctccc attaggccta caatggtgag acaagtagcc    1260
aacagggaag ggttgcaaat atcatttggg cacacctatg ataatattga tgaagcagac    1320
agtattcagc aagtaactga gaggtgggaa gctcaaagcc aaagtcctaa tgtgcagtca    1380
ggtgaattta ttgaaaaatt tgaggctcct ggtggtgcaa atcaaagaac tgctcctcag    1440
tggatgttgc ctttacttct aggcctgtac ggaagtgtta cttctgctct aaaagcttat    1500
gaagatggcc ccaacaaaaa gaaaggaag ttgtccaggg gcagctccca aaaaccaaa     1560 ggaaccagtg caagtgccaa agctcgtcat aaaaggagga atagaagttc taggagttaa    1620
aactggagta gacagcttca ctgaggtgga gtgctttta aatcctcaaa tgggcaatcc    1680
tgatgaacat caaaaaggct taagtaaaag cttagcagct gaaaaacagt ttacagatga    1740
ctctccagac aaagaacaac tgccttgcta cagtgtggct agaattcctt tgcctaattt    1800
aaatgaggac ttaacctgtg gaaatatttt gatgtgggaa gctgttactg ttaaaactga    1860
ggttattggg gtaactgcta tgttaaactt gcattcaggg acacaaaaaa ctcatgaaaa    1920
tggtgctgga aaacccattc aagggtcaaa ttttcatttt tttgctgttg gtggggaacc    1980
tttggagctg cagggtgtgt tagcaaacta caggaccaaa tatcctgctc aaactgtaac    2040
cccaaaaaat gctacagttg acagtcagca gatgaacact gaccacaagg ctgttttgga    2100
taaggataat gcttatccag tggagtgctg ggttcctgat ccaagtaaaa atgaaaacac    2160
tagatatttt ggaacctaca caggtgggga aaatgtgcct cctgttttgc acattactaa    2220
cacagcaacc acagtgcttc ttgatgagca gggtgttggg cccttgtgca agctgacag     2280 cttgtatgtt tctgctgttg acatttgtgg gctgtttacc aacacttctg gaacacagca    2340
gtggaaggga cttcccagat attttaaaat taccccttaga aagcggtctg tgaaaaaccc    2400
ctacccaatt tccttttgt taagtgacct aattaacagg aggacacaga gggtggatgg    2460
gcagcctatg attggaatgt cctctcaagt agaggaggtt agggtttatg aggcacaga     2520 ggagcttcct ggggatccag acatgataag atacattgat gagtttggac aaaccacaac    2580
tagaatgcag tgaaaaaaat gctttatttg tgaaatttgt gatgctattg ctttatttgt    2640
aaccattata agctgcaata aacaagttaa caacaacaat tgcattcatt ttatgtttca    2700
ggttcagggg gaggtgtggg aggttttta aagcaagtaa aacctctaca aatgtggtat    2760
ggctgattat gatcatgaac agactgtgag gactgagggg cctgaaatga gccttgggac    2820
tgtgaatcaa tgcctgttc atgccctgag tcttccatgt tcttctcccc accatcttca    2880 ttttatcag cattttcctg gctgtcttca tcatcatcat cactgtttct tagccaatct    2940
aaaactccaa ttcccatagc cacattaaac ttcatttttt gatacactga caaactaaac    3000
tctttgtcca atctctcttt ccactccaca attctgctct gaatactttg agcaaactca    3060
gccacaggtc tgtaccaaat aacataaga agcaaagcaa tgccactttg aattattctc     3120
ttttctaaca aaaactcact gcgttccagg caatgcttta ataatcttt gggcctaaaa     3180 tctatttgtt ttacaaatct ggcctgcagt gttttaggca cactgtactc attcatggtg    3240
actattccag ggggaaatat ttgagttctt tatttaggt gtttcttttc taagtttacc     3300
ttaacactgc catccaaata atcccttaaa ttgtccaggt tattaattcc ctgacctgaa    3360
ggcaaatctc tggactcccc tccagtgccc tttacatcct caaaaactac taaaaactgg    3420
```

```
tcaatagcta ctcctagctc aaagttcagc ctgtccaagg gcaaattaac atttaaagct    3480
ttccccccac ataattcaag caaagcagct gctaatgtag ttttaccact atcaattggt    3540
cctttaaaca gccagtatct tttttaggaa atgttgtaca ccatgcattt taaaaagtca    3600
tacaccactg aatccatttt gggcaacaaa cagtgtagcc aagcaactcc agccatccat    3660
tcttctatgt cagcagagcc tgtagaacca acattatat ccatcctatc caaaagatca    3720
ttaaatctgt tgttaacat ttgttctcta gttaattgta ggctatcaac ccgcttttta    3780
gctaaaacag tatcaacagc ctgttggcat atggtttttt ggttttgct gtcagcaaat    3840 atagcagcat ttgcataatg cttttcatgg tacttatagt ggctgggctg ttcttttta    3900 atacatttta aacacatttc aaaactgtac tgaaattcca agtacatccc aagcaataac    3960
aacacatcat cacatttgt ttccattgca tactctgtta caagcttcca ggacacttgt    4020
ttagtttcct ctgcttcttc tggattaaaa tcatgctcct ttaacccacc tggcaaactt    4080
tcctcaataa cagaaaatgg atctctagtc aaggcactat acatcaaata ttccttatta    4140
acccctttac aaattaaaaa gctaaaggta cacaattttt gagcatagtt attaatagca    4200
gacactctat gcctgtgtgg agtaagaaaa aacagtatgt tatgattata actgttatgc    4260
ctacttataa aggttacaga atatttttcc ataatttct tgtatagcag tgcagctttt    4320
tcctttgtgg tgtaaatagc aaagcaagca agagttctat tactaaacac agcatgactc    4380
aaaaaactta gcaattctga aggaaagtcc ttggggtctt ctacctttct cttcttttt    4440 ggaggagtag aatgttgaga gtcagcagta gcctcatcat cactagatgg catttcttct    4500
gagcaaaaca ggttttcctc attaaaggca ttccaccact gctcccattc atcagttcca    4560
taggttggaa tctaaaatac acaaacaatt agaatcagta gtttaacaca ttatacactt    4620
aaaaatttta tatttacctt agagctttaa atctctgtag gtagtttgtc caattatgtc    4680
acaccacaga agtaaggttc cttcacaaag atcaagtcca aaccacattc taaagcaatc    4740
gaagcagtag caatcaaccc acacaagtgg atctttcctg tataatttc tattttcatg    4800 cttcatcctc agtaagcaca gcaagcatat gcagttagca gacattttct ttgcacactc    4860
aggccattgt ttgcagtaca ttgcatcaac accaggattt aaggaagaag caaataccctc   4920 agttgcatcc cagaagcctc caaagtcagg ttgatgagca tattttactc catcttccat    4980
tttcttgtac agagtattca ttttcttcat tttttcttca tctcctcctt tatcaggatg    5040
aaactccttg cattttttta aatatgcctt tctcatcaga ggaatattcc cccaggcact    5100
cctttcaaga cctagaaggt ccattagctg caaagattcc tctctgttta aaactttatc    5160
catctttgca aagcttttg caaaagccta ggcctccaaa aaagcctcct cactacttct    5220
ggaatagctc agaggccgag gcg                                           5243
```

<210> SEQ ID NO 2
<211> LENGTH: 288
<212> TYPE: DNA
<213> ORGANISM: Artificial
<220> FEATURE:
<223> OTHER INFORMATION: promoter 1

<400> SEQUENCE: 2

```
agtcagcaac caggtgtgga aagtccccag gctccccagc aggcagaagt atgcaaagca      60
tgcatctcaa ttagtcagca accatagtcc cgccctaac tccgcccatc cgcccctaa      120 ctccgcccag ttccgcccat tctccgcccc atggctgact aattttttttt atttatgcag   180 aggccgaggc cgcctctgcc tctgagctat tccagaagta gtgaggaggc ttttttggag    240
```

```
gcctaggctt tgcaaaaag ctcccgggag cttgtatatc cattttcg      288
```

<210> SEQ ID NO 3
<211> LENGTH: 219
<212> TYPE: DNA
<213> ORGANISM: Artificial
<220> FEATURE:
<223> OTHER INFORMATION: promoter 2

<400> SEQUENCE: 3

```
attagtcagc aaccatagtc ccgcccctaa ctccgcccat ccgccccta actccgccca      60
gttccgccca ttctccgccc catggctgac taatttttt tatttatgca gaggccgagg    120
ccgcctctgc ctctgagcta ttccagaagt agtgaggagg cttttttgga ggcctaggct   180
tttgcaaaaa gctcccggga gcttgtatat ccattttcg                           219
```

<210> SEQ ID NO 4
<211> LENGTH: 172
<212> TYPE: DNA
<213> ORGANISM: Artificial
<220> FEATURE:
<223> OTHER INFORMATION: promoter 3

<400> SEQUENCE: 4

```
ctaactccgc ccagttccgc ccattctccg ccccatggct gactaatttt ttttatttat      60
gcagaggccg aggccgcctc tgcctctgag ctattccaga agtagtgagg aggcttttt    120
ggaggcctag gcttttgcaa aaagctcccg ggagcttgta tatccatttt cg            172
```

<210> SEQ ID NO 5
<211> LENGTH: 348
<212> TYPE: DNA
<213> ORGANISM: Simian virus 40

<400> SEQUENCE: 5

```
ggtgtggaaa gtccccaggc tccccagcag gcagaagtat gcaaagcatg catctcaatt      60
agtcagcaac caggtgtgga agtccccag gctccccagc aggcagaagt atgcaaagca    120
tgcatctcaa ttagtcagca accatagtcc cgcccctaac tccgcccatc cgcccctaa    180
ctccgcccag ttccgcccat tctccgcccc atggctgact aatttttttt atttatgcag   240
aggccgaggc cgcctctgcc tctgagctat tccagaagta gtgaggaggc ttttttggag   300
gcctaggctt tgcaaaaag ctcccgggag cttgtatatc cattttcg                 348
```

<210> SEQ ID NO 6
<211> LENGTH: 146
<212> TYPE: DNA
<213> ORGANISM: Artificial
<220> FEATURE:
<223> OTHER INFORMATION: promoter 4

<400> SEQUENCE: 6

```
tccgccccat ggctgactaa ttttttttat ttatgcagag gccgaggccg cctctgcctc      60
tgagctattc agaagtagt gaggaggctt ttggaggc ctaggctttt gcaaaaagct    120
cccgggagct tgtatatcca ttttcg                                         146
```

<210> SEQ ID NO 7
<211> LENGTH: 717
<212> TYPE: DNA
<213> ORGANISM: Aequorea victoria

<400> SEQUENCE: 7

```
atgagtaaag gagaagaact tttcactgga gttgtcccaa ttcttgttga attagatggt    60
gatgttaatg ggcacaaatt ctctgtcagt ggagagggtg aaggtgatgc aacatacgga   120
aaacttaccc ttaaatttat ttgcactact ggaaagctac ctgttccatg gccaacactt   180
gtcactactt tctcttatgg tgttcaatgc ttttcaagat acccagatca tatgaaacag   240
catgactttt tcaagagtgc catgcccgaa ggttatgtac aggaaagaac tatattttac   300
aaagatgacg ggaactacaa atcacgtgct gaagtcaagt ttgaaggtga taccctcgtt   360
aatagaattg agttaaaagg tattgatttt aaagaagatg aaacattct tggacacaaa    420
atggaataca actataactc acacaatgta tacatcatgg cagacaaaca aaagaatgga   480
atcaaagtta acttcaaaat tagacacaac attgaagatg gaagcgttca actagcagac   540
cattatcaac aaaatactcc aattggcgat ggccctgtcc ttttaccaga caaccattac   600
ctgtccacac aatctgccct ttccaaagat cccaacgaaa agagagatca catgatcctt   660
cttgagtttg taacagctgc tgggattaca catggcatgg atgaactata caaataa      717
```

<210> SEQ ID NO 8
<211> LENGTH: 25
<212> TYPE: DNA
<213> ORGANISM: Artificial
<220> FEATURE:
<223> OTHER INFORMATION: foward primer 1

<400> SEQUENCE: 8

```
ttagggtgtg gaaagtcccc aggct                                          25
```

<210> SEQ ID NO 9
<211> LENGTH: 29
<212> TYPE: DNA
<213> ORGANISM: Artificial
<220> FEATURE:
<223> OTHER INFORMATION: foward primer 2

<400> SEQUENCE: 9

```
aattagtcag caaccaggtg tggaaagtc                                      29
```

<210> SEQ ID NO 10
<211> LENGTH: 25
<212> TYPE: DNA
<213> ORGANISM: Artificial
<220> FEATURE:
<223> OTHER INFORMATION: foward primer 3

<400> SEQUENCE: 10

```
attagtcagc aaccatagtc ccgcc                                          25
```

<210> SEQ ID NO 11
<211> LENGTH: 23
<212> TYPE: DNA
<213> ORGANISM: Artificial
<220> FEATURE:
<223> OTHER INFORMATION: foward primer 4

<400> SEQUENCE: 11

```
ctaactccgc ccagttccgc cca                                            23
```

<210> SEQ ID NO 12
<211> LENGTH: 24
<212> TYPE: DNA
<213> ORGANISM: Artificial

```
<220> FEATURE:
<223> OTHER INFORMATION: forward primer 5

<400> SEQUENCE: 12
ccgccccatg gctgactaat tttt                                              24

<210> SEQ ID NO 13
<211> LENGTH: 22
<212> TYPE: DNA
<213> ORGANISM: Artificial
<220> FEATURE:
<223> OTHER INFORMATION: reverse primer

<400> SEQUENCE: 13
ggagcttgta tatccatttt cg                                                22

<210> SEQ ID NO 14
<211> LENGTH: 72
<212> TYPE: DNA
<213> ORGANISM: Simian virus 40

<400> SEQUENCE: 14
tggttgctga ctaattgaga tgcatgcttt gcatacttct gcctgctggg gagcctgggg       60
actttccaca cc                                                           72
```